United States Patent [19]

Lesher

[11] Patent Number: 4,517,192
[45] Date of Patent: May 14, 1985

[54] 6-ALKYL-5-[4-(ALKYLSULFINYL OR ALKYLSULFONYL)PHENYL]-2(1H)-PYRIDINONES AND THEIR USE AS CARDIATONICS

[75] Inventor: George Y. Lesher, Schodack, N.Y.

[73] Assignee: Sterling Drug Inc., New York, N.Y.

[21] Appl. No.: 462,661

[22] Filed: Jan. 31, 1983

[51] Int. Cl.$^3$ .............. C07D 211/42; C07D 211/86; A61K 31/44

[52] U.S. Cl. .............................. 514/345; 546/288; 546/301; 514/344

[58] Field of Search ............... 546/288, 301; 424/263

[56] References Cited

U.S. PATENT DOCUMENTS

| | | | |
|---|---|---|---|
| 3,655,679 | 4/1972 | Shen et al. | 546/322 |
| 3,718,743 | 2/1973 | Shen et al. | 424/267 |
| 4,276,293 | 6/1981 | Lesher et al. | 424/248.4 |
| 4,312,875 | 1/1982 | Lesher et al. | 424/266 |
| 4,313,951 | 2/1982 | Lesher et al. | 424/263 |

FOREIGN PATENT DOCUMENTS

| | | | |
|---|---|---|---|
| 1238959 | 7/1971 | United Kingdom | 424/263 |
| 2070606 | 9/1981 | United Kingdom | 546/297 |

*Primary Examiner*—Alan L. Rotman
*Attorney, Agent, or Firm*—Robert K. Bair; B. Woodrow Wyatt; Paul E. Dupont

[57] ABSTRACT

3-Q-5-[4-(R'-X)phenyl]-6-R-2(1H)-pyridinones (I), where R and R' are each methyl or ethyl, X is sulfinyl when Q is hydrogen or cyano, or X is sulfonyl when Q is cyano, their preparation and cardiotonic use are shown. Also shown are intermediates 5-[4-(R'-thio)-phenyl]-6-R-2(1H)-pyridinones (II) and also corresponding 3-cyano intermediates.

11 Claims, No Drawings

6-ALKYL-5-[4-(ALKYLSULFINYL OR ALKYLSULFONYL)PHENYL]-2(1H)-PYRIDINONES AND THEIR USE AS CARDIATONICS

BACKGROUND OF THE INVENTION

1. Field of the Invention

This invention relates to selected 6-alkyl-5-[4(alkylsulfinyl or alkylsulfonyl)phenyl]-2(1H)-pyridinones, their use as cardiotonics and their preparation.

2. Description of the Prior Art

Shen et al [U.S. Pat. No. 3,655,679, issued Apr. 11, 1972] show as anti-inflammatory agents various arylhydroxy-pyridinecarboxylic acids including 5-aryl-2-hydroxynicotinic acids where aryl is, inter alia, phenyl containing one or more R substituents which may be at any position on the ring (preferably at the 4-position), said substituents including "alkyl . . . , alkenyl . . . , halogen . . . , haloalkyl . . . , hydroxy, alkoxy . . . , acyloxy . . . , nitro, amino, alkylamino . . . , dialkylamino . . . , acylamino . . . , mercapto, alkylthio (preferably lower alkylthio such as methylthio, ethylthio, etc.), alkylsulfonyl (preferably lower alkylsulfonyl such as methylsulfonyl), or alkylsulfinyl (preferably lower alkylsulfinyl such as methylsulfinyl)". Shown in Table I of Example 55 is 5-(p-methylthiophenyl)-2-hydroxynicotinic acid. Shown as intermediates for these 5-aryl-2-hydroxynicotinic acids, which tautomerically can be designated as 3-carboxy-5-aryl-2(1H)-pyridinones, are various 5-aryl-2-hydroxynicotinonitriles (Table I of Example 48 where aryl is shown, inter alia, to be p-mercaptophenyl and p-methylsulfonylphenyl). Also shown as intermediates for said acids are various methyl 5-aryl-2-hydroxy-6-methylnicotinates (Table I of Example 50 where aryl is shown, inter alia, to be p-methoxyphenyl) and corresponding 5-aryl-2-hydroxy-6-methylnicotinonitriles (last paragraph of Example 50). Also shown in this patent (paragraph common to columns 50 and 51) is the oxidation of 2-(4-methylthiophenyl)-5-hydroxyisonicotinic acid with sodium metaperiodate to produce 2-(4-methylsulfinylphenyl)-5-hydroxyisonicotinic acid.

Shen et al [U.S. Pat. No. 3,718,743, issued Feb. 27, 1973] show "5-phenyl-2-piperidinones and 5-phenyl-2-thiopiperidinones in compositions and methods for treating pain, fever and inflammation". The generic teaching of these piperidinones shows that "phenyl" can have one or two substituents at positions 2, 3, 4, 5 and/or 6, including alkyl, halogen, haloalkyl, aryl, nitro, amino, acylamino, acyl, carboxy, carbalkoxy, carbamyl, dialkylsulfamyl, alkylamino, dialkylamino, alkylmercapto, alkylsulfinyl and alkylsulfonyl. Various means of preparing the 5-phenyl-2-piperidinone final products are shown. In one procedure, a 2-chloro-5-phenylpyridine is heated with aqueous sodium hydroxide in dimethylformamide to produce the corresponding 5-phenyl-2(1H)-pyridinones which are then hydrogenated to produce the desired 5-phenyl-2-piperidinones. Among the intermediate 5-phenyl-2(1H)-pyridinones specifically shown is 5-(4-methoxyphenyl)-2(1H)-pyridinone and its conversion by heating with pyridine hydrochloride under nitrogen to produce the corresponding 5-(4-hydroxyphenyl)-2(1H)-pyridinone.

Merck and Co. [British Pat. No. 1,238,959, published July 14, 1971] show as antiinflammatory agents 3(or 4)-aryl-2(1H)-pyridinones where "aryl" is, inter alia, phenyl which can be mono- or di-substituted by a variety of groups including "alkyl, phenyl, halogen, trihaloalkyl, alkoxy, amino, dialkylamino, nitro, cyano, sulfamoyl, alkylsulfamoyl, dialkylsulfamoyl, hydroxy, mercapto, alkylthio, alkylsulfinyl, alkylsulfonyl, carbamoyl, carboxy, sulfo or phenylsulfonyl". Specifically shown, inter alia, as Examples 33 and 34 are 3-(4-methylsulfinylphenyl)-2(1H)-pyridinone and 3-(4-methylsulfonylphenyl)-2(1H)-pyridinone, which were prepared by oxidation of 3-(4-methylthiophenyl)-2(1H)-pyridinone with sodium metaperiodate and aqueous hydrogen peroxide, respectively.

Sandoz AG [U.K. Patent Application No. 2,070,606, published Sept. 9, 1981] show as intermediates 3-cyano-6-$R_2$-5-aryl-2(1H)-pyridinones where $R_2$ is hydrogen or lower-alkyl and aryl is, inter alia, 4-methoxyphenyl. These compounds are reportedly prepared by reacting cyanoacetamide with 4-dimethylamino-3-aryl-3-buten-2-one and are converted in turn to the corresponding 3-carbamyl and then 3-amino compounds, the latter compounds reported to be cardiotonic agents.

Lesher, Opalka and Page [U.S. Pat. No. 4,276,293, issued June 30, 1981] show as intermediates 3-cyano-6-(lower-alkyl)-5-(pyridinyl)-2(1H)-pyridinones which are prepared by reacting a 1-(pyridinyl)-2-(dimethylamino)ethenyl lower-alkyl ketone with α-cyanoacetamide and conversion thereof, by hydrolysis and decarboxylation, to the corresponding 6-(lower-alkyl)-5-(pyridinyl)-2(1H)-pyridinones.

Lesher and Philion [U.S. Pat. No 4,313,951, issued Feb. 2, 1982 from application Ser. No. 198,461, filed Oct. 20, 1980 as a continuation-in-part of application Ser. No. 97,504, filed Nov. 26, 1979 and now abandoned] disclose as cardiotonics, inter alia, 3-cyano-6-(lower-alkyl)-5-(pyridinyl)2(1H)-pyridinones and their preparation, and also the conversion by hydrolysis of said 3-cyano compounds to the corresponding 3-carbamyl compounds and subsequent conversion of the latter to the corresponding cardiotonically active 3-amino-6-(lower-alkyl)-5-(pyridinyl)-2(1H)-pyridinones.

Lesher, Opalka and Page [U.S. Pat. No. 4,312,875, issued Jan. 26, 1982] disclose 6-(lower-alkyl)-5-(pyridinyl)-2(1H)-pyridinones as cardiotonics.

SUMMARY OF THE INVENTION

In a composition of matter aspect, the invention resides in 3-Q-5-[4-(R'-X)phenyl]-6-R-2(1H)-pyridinones (I), useful as cardiotonic agents, where Q, R, R' and X are defined hereinbelow.

A composition aspect of the invention resides in a cardiotonic composition for increasing cardiac contractility in a patient, said composition comprising a pharmaceutically acceptable carrier and, as the active ingredient, a cardiotonically effective amount of said 3-Q-5-[4-(R'-X)phenyl]-6-R-2(1H)-pyridinone (I).

A method aspect of the invention resides in the method for increasing cardiac contractility in a patient requiring such treatment which comprises administering a medicament comprising a pharmaceutically acceptable carrier and, as the active component, a cardiotonically effective amount of said 3-Q-5-[4-(R'-X)phenyl]-6-R-2(1H)-pyridinone (I).

A process aspect of the invention resides in the process which comprises reacting 3-Q-5-[4-(R'-thio)-phenyl]-6-R-2(1H)-pyridinone with a reagent capable of oxidizing sulfides to sulfoxides to produce 3-Q-5-[4-(R'-sulfinyl)phenyl]-6-R-2(1H)-pyridinone where Q, R and R' are defined hereinbelow.

In another process aspect the invention resides in the process for preparing 3-cyano-5-[4-(R'-sulfonyl)phenyl]-6-R-2(1H)-pyridinone which comprises reacting 3-cyano-5-[4-(R'-sulfinyl)phenyl]-6-R-2(1H)-pyridinone with a reagent capable of oxidizing sulfoxides to sulfones or by reacting 3-cyano-5[4-(R'-thio)phenyl]-6-R-2(1H)-pyridinone with a reagent capable of oxidizing sulfides to sulfones, where R and R' have the meanings given below.

Another composition of matter aspect of the invention resides in 5-[4-(R'-thio)phenyl]-6-R-2(1H)-pyridinones (II), useful as intermediates, where R' and R are defined hereinbelow.

DETAILED DESCRIPTION INCLUSIVE OF PREFERRED EMBODIMENTS

A composition of matter aspect of the invention resides in a 3-Q-5-[4-(R'-X)phenyl]-6-R-2(1H)-pyridinone having formula I

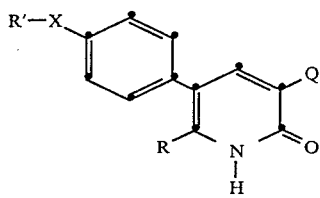

I where R and R' are each methyl or ethyl, X is sulfinyl when Q is hydrogen or cyano, or X is sulfonyl when Q is cyano. The compounds of formula I are useful as cardiotonics, as determined by standard pharmacological evaluation procedures. Preferred embodiments are those of formula I where Q is hydrogen, X is sulfinyl, R' is methyl and R is methyl or ethyl. A particularly preferred embodiment is 6-methyl-5-[4-(methylsulfinyl)phenyl]-2(1H)-pyridinone.

A composition aspect of the invention resides in a cardiotonic composition for increasing cardiac contractility, said composition comprising a pharmaceutically acceptable carrier and, as the active component thereof, a cardiotonically effective amount of the compound of formula I where R', X, R and Q are defined as in formula I. Preferred embodiments of this composition aspect of the invention are those where the active component is the compound of formula I where Q is hydrogen, X is sulfinyl, R' is methyl and R is methyl or ethyl; and, a particularly preferred active component is 6-methyl-5-[4-(methylsulfinyl)phenyl]-2(1H)-pyridinone.

A method aspect of the invention resides in the method for increasing cardiac contractility in a patient requiring such treatment which comprises administering orally or parenterally in a solid or liquid dosage form to such patient a composition comprising a pharmaceutically acceptable carrier and, as active component thereof, a cardiotonically effective amount of the compound of formula I where R', X, R and Q are defined as in formula I. Preferred embodiments and a particularly preferred embodiment of this method aspect of the invention are those where the active component is the same as the active component of the respective preferred and particularly preferred composition embodiments described in the immediately preceding paragraph.

A process aspect of the invention for preparing the compound according to formula I where X is sulfinyl resides in the process which comprises reacting 3-Q-5-[4-(R'-thio)phenyl]-6-R-2(1H)-pyridinone with a reagent capable of oxidizing sulfides to sulfoxides to produce 3-Q-5-[4-(R'-sulfinyl)phenyl]-6-R-2(1H)-pyridinone having formula I where X is sulfinyl. Preferred embodiments are those which produce 5-[4-(methylsulfinyl)phenyl]-6-(methyl or ethyl)-2(1H)-pyridinone.

In another process aspect the invention resides in the process for preparing the compound according to formula I where X is sulfonyl and Q is cyano which comprises either reacting 3-cyano-5-[4-(R'-thio)phenyl]-6-R-2(1H)-pyridinone with at least two molar equivalents of a reagent capable of oxidizing sulfides to sulfones or reacting 3-cyano-5-[4-(R'-sulfinyl)phenyl]-6-R-2(1H)pyridinone with one molar equivalent of a reagent capable of oxidizing sulfoxides to sulfones to produce 3-cyano-5-[4-(R'-sulfonyl)phenyl]-6-R-2(1H)-pyridinone having formula I where X is sulfonyl, Q is cyano, and R' and R have the meanings given for formula I.

Another composition of matter aspect of the invention resides in a 5-[4-(R'-thio)phenyl]-6-R-2(1H)-pyridinone having formula II

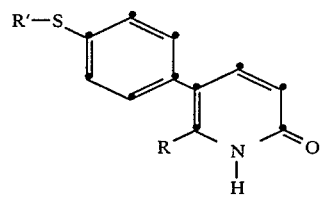

II where R' and R are each methyl or ethyl. These compounds are useful for preparing the compounds of formula I where X is sulfinyl and Q is hydrogen. Preferred embodiments are those where R' is methyl; and, a particularly preferred embodiment is 6-methyl-5-[4-(methylthio)phenyl]-2(1H)-pyridinone.

The molecular structures of the compounds of formulas 1 and 2 were assigned on the basis of evidence provided by infrared, nuclear magnetic resonance and mass spectra, and by the correspondence of calculated and found values for the elemental analyses.

The manner of making and using the instant invention will now be generally described so as to enable a person skilled in the art of pharmaceutical chemistry to make and use the same.

The oxidation of 3-Q-5-[4-(R'-thio)phenyl]-6-R-2(1H)-pyridinone to produce the corresponding 3-Q-5-[4-(R'-sulfinyl)phenyl]-6-R-2(1H)-pyridinone (Formula I where X is sulfinyl) is carried out by reacting said 4-(R'-thio) compound with an equimolar quantity of an oxidizing agent effective to oxidize sulfides to sulfoxides such as hydrogen peroxide or a per-organic acid, e.g., peracetic acid, perbenzoic acid, in a suitable solvent. In practicing the invention a convenient procedure utilized hydrogen peroxide in acetic acid at room temperature followed by gentle heating of the reaction mixture on a steam bath for a short period. If tlc analysis of the reaction mixture showed the presence of starting 4-(R'-thio) compound, an additional small quantity of oxidizing agent, e.g., hydrogen peroxide, was added and the reaction mixture gently heated again.

The oxidation of 3-cyano-5-[4-(R'-thio)phenyl]-6-R-2(1H)-pyridinone to produce 3-cyano-5-[4-(R'-sulfonyl)phenyl]-6-R-2(1H)-pyridinone (Formula I where X is sulfonyl) is carried out by reacting said 4-(R'-thio) compound with at least two molar equivalents of an oxidizing agent per mole of 4-(R'-thio) compound, said oxidizing agent effective to oxidize sulfides to sulfones, such as hydrogen peroxide or a per-organic acid in a suitable solvent, such as given above. Optionally, the conversion of 4-(R'-thio) compound to 4-(R'-sulfonyl) compound can be carried out using hydrogen peroxide or per-organic acid in the presence of a small quantity of a catalyst such as tungstic acid. Other oxidizing agents capable of forming the 4-(R'-sulfonyl) compounds include chromic trioxide ($CrO_3$), potassium permanganate, and the like. Alternatively, said 4-(R'-sulfinyl) compounds can be oxidized to the corresponding 4-(R'-sulfonyl) compounds using at least one molar equivalent of oxidizing agent per mole of 4-(R'-sulfinyl) compound and the same oxidative reaction conditions for converting said 4-(R'-thio) compounds to said 4-(R'-sulfonyl) compounds.

The intermediate 3-cyano-5-[4-(R'-thio)phenyl]-6-R-2(1H)-pyridinones are prepared by generally known methods such as those illustrated hereinbelow.

The conversion of the intermediate 3-cyano-5-[4-(R'-thio)phenyl]-6-R-2(1H)-pyridinones to the corresponding intermediate 5-[4-(R'-thio)phenyl]-6-R-2(1H)-pyridinones by heating the 3-cyano compound with an acid such as 85% phosphoric acid or concentrated sulfuric acid resulting first in hydrolysis of 3-cyano to 3-carboxy and then in decarboxylation of 3-carboxy is generally known and is illustrated hereinbelow.

A. 1-[4-(R'-THIO)-PHENYL]-2-ALKANONES

A-1. 1-[4-(Methylthio)phenyl]-2-propanone—A stirred mixture containing 15.7 g of 1-[4-(methylthiophenyl]-2-nitro-1-propene, 25.2 g of reduced iron, 100 ml of water and 20 ml of toluene was brought to reflux. To the stirred reaction mixture was added dropwise over a 10 minute period 15 ml of concentrated hydrochloric acid resulting in a vigorous exothermic reaction whereupon the heat source was removed. The reaction mixture was then refluxed for 90 minutes, the heat source removed and 23 g of sodium bicarbonate added portionwise. The resulting mixture was refluxed with stirring for 10 minutes and then cooled. About 50 ml of ether was added, the mixture stirred for 10 minutes and then filtered through diatomaceous earth, washing the filter pad with ether. The ether layer was separated; the water layer was washed twice with ether; and, the ether layers were combined and dried over anhydrous sodium sulfate. Removal of the ether in vacuo yielded 13.5 g of 1-[4-(methylthio)phenyl]-2-propanone. The above 13.5 g of product was combined with another 31 g of the same material obtained in other runs and the combined product was distilled under reduced pressure to yield 25 g of 1-[4-(methylthio)phenyl]-2-propanone, b.p. 100°–104° C. at 0.15–0.20 mm.

The intermediate 1-[4-(methylthio)phenyl]-2-nitro-1-propene was prepared as follows: [U.S. Pat. No. 3,117,160, Example V]; a mixture containing 15.2 g of 4-(methylthio)benzaldehyde, 7.5 g of nitroethane, 0.73 g of n-butylamine and 40 ml of absolute ethanol was refluxed with stirring for 21 hours and the solvent then removed by distilling in vacuo. The residue was recrystallized from absolute ethanol (total volume of 60 ml) washed with a small quantity of cold ethanol and dried in vacuo at room temperature to produce 9.3 g of 1-[4-(methylthio)phenyl]-2-nitro-1-propene, m.p. 74°–76° C.

Following the procedure described in the immediately preceding paragraph for preparing 1-[4-(methylthio)phenyl]-2-nitro-1-propene using in place of 4-methylthiobenzaldehyde and/or nitroethane molar equivalent quantities respectively of 4-(methylthio or ethylthio)benzaldehyde and/or nitroethane or nitropropane, it is contemplated that the following compounds can be obtained: 1-[4-(ethylthio)phenyl]-2-nitro-1-propene using 4-(ethylthio)benzaldehyde and nitroethane; 1-[4-(methylthio)phenyl]-2-nitro-1-butene using 4-(methylthio)benzaldehyde and 1-nitropropane; and, 1-[4-(ethylthio)phenyl]-2-nitro-1-butene using 4-(ethylthio)benzaldehyde and 1-nitropropane.

Following the procedure described in Example A-1 using in place of 1-[4-(methylthio)phenyl]-2-nitro-1-propene a molar equivalent quantity of the corresponding 1-[4-(methyl-or ethylthio)phenyl]-2-nitro-1-propene or -1-butene, it is contemplated that the corresponding compounds of Examples A-2, A-3 and A-4 can be obtained.

A-2. 1-[4-(Ethylthio)phenyl]-2-propanone, using 1-[4-(ethylthio)phenyl]-2-nitro-1-propene.

A-3. 1-[4-(Methylthio)phenyl]-2-butaneone, using 1-[4-(methylthio)phenyl]-2-nitro-1-butene.

A-4. 1-[4-(Ethylthio)phenyl]-2-butanone, using 1-[4-(ethylthio)phenyl]-2-nitro-1-butene.

B. 3-Q-5-[4-(R'-X)-PHENYL]-6-R-2(1H)-PYRIDINONES

B-1. 3-Cyano-6-methyl-5-[4-(methylthio)phenyl]-2(1H)-pyridinone, alternatively named 1,2-dihydro-6-methyl-5-[4-(methylthio)phenyl]-2-oxo-3-pyridinecarbonitrile—A solution containing 36.0 g of 1-[4-(methylthio)phenyl]-2-propanone, 32.2 g of dimethylformamide dimethylacetyl and 50 ml of dimethylformamide was stirred at room temperature for 8 hours and then allowed to stand at room temperature overnight. The reaction mixture was heated with stirring on a steam bath for 90 minutes and stripped under high vacuum to produce 48.2 g of an oil, which solidified. The solid was dissolved in 100 ml of hot isopropyl acetate; the solution was diluted slowly with n-hexane while heating on a steam bath until the appearance of an oily material (total volume of about 400 ml); and, the hot mixture was cooled while scratching the inner walls of the container with a glass rod to induce precipitation. The mixture was cooled in a freezer overnight to complete precipitation. The solid that separated was collected, washed successively with cold isopropyl acetate and n-hexane, sucked dry and dried in vacuo at 55° C. to yield 43.9 g of 4-(dimethylamino)3-[4-(methylthio)phenyl]-3-buten-2-one, m.p. 89°–91° C. A 12.6 g portion of cyanoacetamide was added to a stirred suspension containing 13.5 g of sodium methoxide and 65 ml of dimethylformamide at room temperature and the resulting solution was cooled slightly. To the solution was added portionwise 23.5 g of 4-(dimethylamino)-3-[4-(methylthio)phenyl]-3-buten-2-one followed by an additional 65 ml of dimethylformamide. The resulting reaction mixture was heated with stirring on a steam bath for 12 hours and then poured into 600 ml of water. The mixture containing some solid was made acidic with 20 ml of glacial acetic acid; the resulting mixture was stirred and allowed to stand for 30 minutes. The separated solid was collected, washed with water, sucked dry and dried at 85° C. in vacuo to yield 24.5 g of product m.p. 272°–274° C. The product was slurried with hot absolute ethanol (total volume of 150 ml) on a steam bath for 30 minutes (very little dissolved) and the mixture cooled in an ice bath. The solid was collected, washed with cold absolute ethanol, sucked dry, and dried in vacuo at 65° C. to yield 23.3 g of 3-cyano-6-methyl-5-[4-(methylthio)phenyl]-2(1H)-pyridinone, m.p. 275°–276° C.

Following the procedure described in Example B-1 using in place of 1-[4-(methylthio)phenyl]-2-propanone a molar equivalent quantity of the appropriate 1-[4-(methyl or ethylthio)phenyl]-2-propanone or -2-butanone, it is contemplated that the corresponding compounds of Examples B-2 through B-4 can be obtained.

B-2. 3-Cyano-5-[4-(ethylthio)phenyl]-6-methyl-2(1H)-pyridinone, using 1-[4-(ethylthio)phenyl]-2-propanone.

B-3. 3-Cyano-6-ethyl-5-[4-(methylthio)phenyl]-2(1H)-pyridinone, using 1-[4-(methylthio)phenyl]-2-butanone.

B-4. 3-Cyano-6-ethyl-5-[4-(ethylthio)phenyl]-2(1H)-pyridinone, using 1-[4-(ethylthio)phenyl]-2-butanone B-5. 6-Methyl-5-[4-(methylthio)phenyl]-2(1H)-pyridinone—A mixture containing 5.12 g of 3-cyano-6-methyl-5-[4-(methylthio)phenyl]-2(1H)-pyridinone and 100 ml of 85% phosphoric acid was refluxed with stirring for 4 hours and then cooled to room temperature. The reaction mixture was added to a mixture of 600 ml of ice and water. The mixture was allowed to stand for about 1 hour and then the precipitate was collected, washed with water, dried at 65° C. in vacuo to yield 4.6 g of material, m.p. 170°–180° C. The solid was pulverized and slurried with 400 ml of water plus 5 g of sodium bicarbonate at 95°–100° C. for 1 hour. The insoluble material was collected, washed with hot water and dried at 65° C. in vacuo to yield 3.4 g of material, m.p. 196°–210° C. The 3.4 g of material was combined with another 8.2 g of material obtained in several other runs and the combined 11.6 g of solid was dissolved in about 300 ml of boiling isopropyl alcohol, the hot solution treated with decolorizing charcoal and filtered, the filtrate concentrated to a volume of about 200 ml and then allowed to cool. The white solid precipitate was collected, washed with cold isopropyl alcohol, dried at 65° C. in vacuo to yield 9.9 g of 6-methyl-5-[4-(methylthio)phenyl]-2(1H)-pyridinone, m.p. 211°–212° C.

Following the procedure described in Example B-5 using in place of 3-cyano-6-methyl-5-(4-(methylthio)phenyl]-2(1H)-pyridinone a molar equivalent quantity of the appropriate 3-cyano-6-(methyl or ethyl)-5-[4-(methylthio or ethylthio)phenyl]-2(1H)-pyridinone, it is contemplated that the compounds of Examples B-6, B-7 and B-8 can be obtained.

B-6. 5-[4-(Ethylthio)phenyl]-6-methyl-2(1H)-pyridinone, using 3-cyano-5-[4-(ethylthio)phenyl]-6-methyl-2(1H)-pyridinone.

B-7. 6-Ethyl-5-(4-(methylthio)phenyl]-2(1H)-pyridinone, using 3-cyano-6-ethyl-5-[4-(methylthio)phenyl]-2(1H)-pyridinone.

B-8. 6-Ethyl-5-(4-(ethylthio)phenyl]-2(1H)-pyridinone, using 3-cyano-6-ethyl-5-[4-(ethylthio)phenyl]-2(1H)-pyridinone.

B-9. 3-Cyano-6-methyl-5-[4-(methylsulfinyl)phenyl]-2(1H)-pyridinone, alternatively named 1,2-dihydro-6-methyl-5-[4-(methylsulfinyl)phenyl]-2-oxo-3-pyridinecarbonitrile—A stirred mixture containing 5.12 g of 3-cyano-6-methyl-5-[4-(methylthio)phenyl]-2(1H)-pyridinone and 200 ml of glacial acetic acid was heated gently on a steam bath to complete solution. The mixture was then allowed to cool to room temperature and to it was added dropwise over a period of 20 minutes 0.68 g of hydrogen peroxide in acetic acid (33.12 mg/ml/20.5 ml). After addition had been completed, the reaction mixture was stirred at room temperaure for 30 minutes, then heated gently on a steam bath for 15 minutes, and then cooled to room temperature. An additional 0.3 ml of said hydrogen peroxide solution was added, the mixture heated gently with stirring on a steam bath for 15 minutes and then stripped in vacuo to yield 5.9 g of solid residue. The residue was suspended and slurried in 400 ml of boiling absolute ethanol. Dimethylformamide was added portionwise until dissolution, while maintaining a constant volume by occasional addition of absolute ethanol, and the mixture was then cooled. The separated solid was collected, washed with a small quantity of cold absolute ethanol, and dried in vacuo at 65° C. to yield 4.0 g of 3-cyano-6-methyl-5-[4-(methylsulfinyl)phenyl]-2(1H)-pyridinone, m.p. 290°–291° C. with decomposition.

Following the procedure described in Example B-9 using in place of 3-cyano-6-methyl-5-[4-(methylthio)phenyl]-2(1H)-pyridinone a molar equivalent quantity of the appropriate 3-cyano-6-(methyl or ethyl)-5-[4-(methylthio or ethylthio)phenyl]-2(1H)-pyridinone, it is contemplated that the corresponding 3-cyano-6-(methyl or ethyl)-5-[-4-(methylsulfinyl or ethylsulfinyl)phenyl]-2(1H)pyridinones of Examples B-10, B-11 and B-12 can be obtained.

B-10. 3-Cyano-5-[4-(ethylsulfinyl)phenyl]-6-methyl-2(1H)-pyridinone, using 3-cyano-5-[4-(ethylthio)phenyl]-2(1H)-pyridinone.

B-11. 3-Cyano-6-ethyl-5-[4-(methylsulfinyl)phenyl]-2(1H)-pyridinone, using 3-cyano-6-ethyl-5-[4-(methylthio)phenyl]-2(1H)-pyridinone.

B-12. 3-Cyano-6-ethyl-5-(4-(ethylsulfinyl)phenyl]-2(1H)-pyridinone, using 3-cyano-6-ethyl-5-[4-(ethylthio)phenyl]-2(1H)-pyridinone.

B-13. 6-Methyl-5-[4-(methylsulfinyl)phenyl]-2(1H)-pyridinone—To a stirred solution containing 4.66 g of 6-methyl-5-[4-(methylthio)phenyl]-2(1H)-pyridinone and 100 ml of glacial acetic acid at room temperature was added dropwise over a period of 25 minutes a solution containing 0.68 g of hydrogen peroxide in acetic acid (33.12 mg/ml/20.50 ml). After said addition had been completed, the mixture was stirred at room temperature for 30 minutes and then heated gently on a steam bath for 15 minutes and cooled. To the reaction mixture was added an additional 0.15 ml of said hydrogen peroxide solution, the resulting mixture heated for 15 minutes and then stripped under high vacuum. The remaining solid residue was dissolved in about 350 ml of boiling absolute ethanol, the solution concentrated to a volume of 75 ml and then cooled to complete precipitation of the product. The precipitate was collected, dried in vacuo at 65° C. to yield 4.6 g of 6-methyl-5-[4-(methylsulfinyl)phenyl]-2(1H)-pyridinone, m.p. 262°–264° C.

Following the procedure described in Example B-13 using in place of 6-methyl-5-[4-(methylthio)phenyl]-2(1H)-pyridinone a molar equivalent quantity of the appropriate 6-(methyl or ethyl)-5-[4-(methylthio or ethylthio)phenyl]-2(1H)-pyridinone, it is contemplated that the following compounds of Examples B-14, B-15 and B-16 can be obtained.

B-14. 5-[4-(Ethylsulfinyl)phenyl]-6-methyl-2(1H)-pyridinone, using 5-[4-(ethylthio)phenyl]-6-methyl-2(1H)-pyridinone.

B-15. 6-Ethyl-5-[4-(methylsulfinyl)phenyl]-2(1H)-pyridinone, using 6-ethyl-5-(4-(methylthio)phenyl]2(1H)-pyridinone.

B-16. 6-Ethyl-5-(4-(ethylsulfinyl)phenyl]-2(1H)-pyridinone, using 6-Ethyl-5-[4-(ethylsulfinyl)phenyl]-2(1H)-pyridinone.

B-17. 3-Cyano-6-methyl-5-[4-(methylsulfonyl)phenyl]-2(1H)-pyridinone—A solution containing 5.44 g of 3-cyano-6-methyl-5-[4-(methylthio)phenyl]-2(1H)-pyridinone and 200 ml of glacial acetic acid was heated with stirring until dissolution resulted and the solution cooled slightly. To the solution was added 500 mg of tungstic acid and the resulting mixture was added dropwise over a period of 30 minutes a solution containing 1.36 g of hydrogen peroxide in glacial acetic acid (b 32.97 mg/ml41.2 ml) and then the mixture was heated occasionally over a period of 1 hour followed by an additional heating period for 1 hour. After tlc analysis showed the reaction to be incomplete, another 5 ml of said hydrogen peroxide solution was added and with stirring and the mixture heated for another hour. Since the reaction was still incomplete, as indicated by tlc analysis, another 5 ml of said hydrogen peroxide solution was added and the resulting mixture heated with stirring for another hour. The reaction mixture was filtered hot to remove the tungstic acid, the filtrate was stripped in vacuo to a volume of about 150 ml, and the resulting concentrate was allowed to cool. The separated product was collected, washed with ethanol and dried in vacuo at 65° C. to yield 5.2 g of 3-cyano-6-methyl-5-[4-(methylsulfonyl)phenyl]-2(1H)-pyridinone, m.p. 312°–313° C.

The above 4-(methylsulfonyl)phenyl compound also was prepared from the corresponding 4-(methylsulfinyl)phenyl compound as follows: to a stirred warm solution containing 0.8 g of 3-cyano-6-methyl-5-[4-(methylsulfinyl)phenyl]-2(1H)-pyridinone in 30 ml of glacial acetic acid was added 500 ml tungstic acid and to the resulting stirred solution was added dropwise over a period of 2 minutes a solution containing 0.102 g of hydrogen peroxide in acetic acid (32.97 mg/ml/3.1 ml) and the resulting reaction mixture was stirred at room temperature for 1 hour and then heated occasionally over a period of 1 hour. After tlc analysis indicated a small quantity of methylsulfinyl compound still present, and additional 3 ml of said hydrogen peroxide solution was added and heating as above was continued for 1 hour. The hot reaction mixture was filtered thru diatomaceous earth to remove the tungstic acid, the filter pad washed with warm acetic acid and the filtrate stripped, first in vacuo and then under high vacuum. The remaining solid residue was slurried in about 75 ml of hot absolute ethanol and the mixture cooled slightly. The solid was collected, washed with ethanol and dried at 65° C. in vacuo to yield 0.7 g of 3-cyano-6-methyl-5-[4-(methylsulfonyl)phenyl]-2(1H)-pyridinone, m.p. 311°–313° C.

Following the procedures described in Example B-17 using in place of 3-cyano-6-methyl-5-[4-(methylthio or methylsulfinyl)phenyl]-2(1H)-pyridinone, it is contemplated that the corresponding 3-cyano-6-(ethyl or methyl)-5-[4-(methylsulfonyl or ethylsulfonyl)phenyl]-2(1H)-pyridinones of Examples B-18, B-19 and B-20 can be obtained.

B-18. 3-Cyano-5-[4-(ethylsulfonyl)phenyl]-6-methyl-2(1H)-pyridinone, using 3-cyano-5-[4-(ethylthio)phenyl]-6-methyl-2(1H)-pyridinone or 3-cyano-5-[4-(ethylsulfinyl)phenyl]-6-methyl-2(1H)-pyridinone.

B-19. 3-Cyano-6-ethyl-5-[4-(methylsulfonyl)phenyl]-2(1H)-pyridinone, using 3-cyano-6-ethyl-5-(4-(methylthio)phenyl]-2(1H)-pyridinone or 3-cyano-6-ethyl-5-[4-(methylsulfinyl)phenyl]-2(1H)-pyridinone.

B-20. 3-Cyano-6-ethyl-5-[4-(ethylsulfonyl)phenyl]-2(1H)-pyridinone, using 3-cyano-6-ethyl-5-(4-(ethylthio)phenyl]-2(1H)-pyridinone or 3-cyano-6-ethyl-5-[4-(ethylsulfinyl)phenyl]-2(1H)-pyridinone.

The utility of the compounds of formula I as cardiotonic agents is demonstrated by their effectiveness in standard pharmacological test procedures, for example, in causing a significant increase in contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat or guinea pig atria and papillary muscle procedure, the compounds of the invention at doses of 1, 3, 10 and/or 30 $\mu$g/ml., were found to cause significant increases, that is, greater than 25% (cat) or 30% (g. pig) in papillary muscle force and significant increases, that is greater than 25% (cat) or 30% (g. pig) in right atrial force, while causing a lower percentage increase (about one-half or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, illustrative guinea pig papillary muscle and right atrial force increases for compounds of the invention are: 100% and 82% at 10 $\mu$g/ml, 97% and 98% at 3 $\mu$g/ml and 64% and 64% at 1 $\mu$g/ml for the compound of Example B-13; 76% and 78% at 10 $\mu$g/ml for the compound of Example B-9; and, 70% and 59% at 10 $\mu$g/ml for the compound of Example B-17.

When tested by said anesthetized dog procedure, the compounds of the invention at doses of 30, 100 and/or 300 $\mu$g/kg administered intravenously were found to cause significant increases, that is, 25% or greater, in cardiac contractile force or cardiac contractility with lower changes in heart rate and blood pressure. For example, the compound of Example B-13 was found to cause respective increases of 42%, 91% and 153% in contractile force (cf) at doses of 30, 100 and 300 $\mu$g/kg.

The present invention includes within its scope a cardiotonic composition for increasing cardiac contractility, said composition comprising a pharmaceutically acceptable carrier and, as the active component thereof, a cardiotonically effective amount of the compound of formula I. The invention also includes within its scope the method for increasing cardiac contractility in a patient requiring such treatment which comprises administering to such patient said cardiotonic composition providing a cardiotonically effective amount of the said compound of formula I. In clinical practice said compound will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueousorganic and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

I claim:

1. 3-Q-5-[4-(R'-X)phenyl]-6-R-2(1H)-pyridinone having the formula

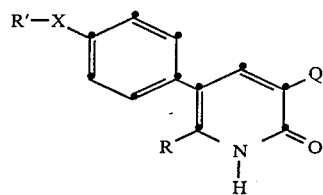

where R and R' are each methyl or ethyl, X is sulfinyl when Q is hydrogen or cyano, or X is sulfonyl when Q is cyano.

2. A compound according to claim 1 where Q is hydrogen, R' is methyl, X is sulfinyl and R is methyl or ethyl.

3. 6-methyl-5-[4-(methylsulfinyl)phenyl]-2(1H)-pyridinone according to claim 1.

4. 3-Cyano-6-methyl-5-[4-(methylsulfinyl)phenyl]-2(1H)-pyridinone according to claim 1.

5. 3-Cyano-6-methyl-5-[4-(methylsulfonyl)phenyl]-2(1H)-pyridinone according to claim 1.

6. A cardiotonic composition for increasing cardiac contractility, said composition comprising a pharmaceutically acceptable carrier and, as the active component thereof, a cardiotonically effective amount of the 3-Q-5-[4-(R'-X)phenyl]-6-R-2(1H)-pyridinone according to claim 1 where R, R', X and Q are defined as in claim 1.

7. A composition according to claim 6 where the active component is the compound where Q is hydrogen, R' is methyl, X is sulfinyl and R is methyl or ethyl.

8. A composition according to claim 6 where the active component is 6-methyl-5-[4-(methylsulfinyl)phenyl]-2(1H)-pyridinone 9. The method for increasing cardiac contractility in a patient requiring such treatment which comprises administering orally or parenterally in a solid or liquid dosage form to such patient a cardiotonically effective amount of a composition according to claim 6.

10. The method according to claim 9 where the active component is 6-(methyl or ethyl)-5-[4-(methylsulfinyl)pheny]-b 2(1H)-pyridinone.

11. The method according to claim 9 where the active component is 6-methyl-5-[4-(methylsulfinyl)phenyl]-2(1H)-pyridinone.

* * * * *

UNITED STATES PATENT AND TRADEMARK OFFICE
CERTIFICATE OF CORRECTION

PATENT NO. : 4,517,192

DATED : May 14, 1985

INVENTOR(S) : George Y. Lesher

It is certified that error appears in the above-identified patent and that said Letters Patent is hereby corrected as shown below:

Face page, title "CARDIATONICS" should read -- CARDIOTONICS --.

Column 1, title, line 3, "CARDIATONICS" should read -- CARDIOTONICS --.

Column 1, lines 8-9, "4(alkylsulfinyl" should read -- 4-(alkylsulfinyl --.

Column 3, line 6, "3-cyano-5[" should read -- 3-cyano-5-[ --.

Column 12, Claim 10, line 43, "phenyl]-b 2(1H)-pyridinone" should read -- phenyl]-2(1H)-pyridinone --.

Signed and Sealed this

Twenty-sixth Day of November 1985

[SEAL]

Attest:

DONALD J. QUIGG

Attesting Officer

Commissioner of Patents and Trademarks